United States Patent

Diago et al.

[11] Patent Number: 5,840,885
[45] Date of Patent: Nov. 24, 1998

[54] PROCESSES FOR THE PRODUCTION OF 6-α-AMINOACYL-PENICILLIN AND 7-α-AMINOACYL-DESACETOXYCEPHALOSPORIN DERIVATIVES

[75] Inventors: Jose Diago, Granollers, Spain; Johannes Ludescher, Breitenbach, Austria

[73] Assignee: Biochemie Gesellschaft m.b.H., Kundl, Austria

[21] Appl. No.: 468,148

[22] Filed: Jun. 6, 1995

Related U.S. Application Data

[63] Continuation of Ser. No. 278,772, Jul. 21, 1994, abandoned, which is a continuation of Ser. No. 922,277, Jul. 29, 1992, abandoned, which is a continuation of Ser. No. 643,876, Jan. 18, 1991, abandoned.

[30] Foreign Application Priority Data

Jan. 22, 1990 [AT] Austria ..................................... 127/90

[51] Int. Cl.⁶ ..................... C07D 487/00; C07D 499/04; C07D 501/20
[52] U.S. Cl. ........................... 540/222; 540/221; 540/302
[58] Field of Search ................... 540/221, 222, 540/302

[56] References Cited

U.S. PATENT DOCUMENTS

| | | |
|---|---|---|
| 3,316,247 | 4/1967 | Fosker et al. . |
| 3,971,775 | 7/1976 | Cowley et al. . |
| 4,123,611 | 10/1978 | Ishimaru et al. . |
| 4,128,547 | 12/1978 | van der Drift et al. . |
| 4,193,918 | 3/1980 | Bianchini et al. . |
| 4,299,955 | 11/1981 | Falciani et al. ............................ 544/30 |
| 4,358,588 | 11/1982 | Hannigar et al. . |

FOREIGN PATENT DOCUMENTS

| | | |
|---|---|---|
| 255647 | 7/1967 | Austria . |
| 2120150 | 12/1971 | France . |
| 2822876 | 12/1978 | Germany . |
| 54-059296 | 5/1979 | Japan . |
| 1531384 | 3/1976 | United Kingdom . |
| WO9117166 | 11/1991 | WIPO . |

OTHER PUBLICATIONS

J.L. Spencer, et al., J. Med. Chem. 9, 746 (1966).
J. Cabre–Castellvi, et al., Afinidad 43, 421 (1986.
Chemical Abstracts vol. 106, 1987—106:119004b.
CA 85; 177, 405 s; 1976.
CA 86; 55467 p; 1976.
CA 91; 5236 v; 1978.

*Primary Examiner*—Mukund J. Shah
*Assistant Examiner*—Pavanaram K Sripada
*Attorney, Agent, or Firm*—Michael W. Glynn; Melvyn M. Kassenoff; Thomas O. McGovern

[57] ABSTRACT

A new process is described for the production of 6-alpha-amino-penicillins and 7-alpha-amino-desacetoxy-cephalosporins free from halogen-containing solvents by acylating 6-APA, 7-ADCA or a derivative thereof in a halogen-free solvent.

18 Claims, No Drawings

PROCESSES FOR THE PRODUCTION OF 6-α-AMINOACYL-PENICILLIN AND 7-α-AMINOACYL-DESACETOXYCEPHALOSPORIN DERIVATIVES

This is a continuation of application Ser. No. 08/278,772, filed Jul. 21, 1994, abandoned, which in turn is a continuation of application Ser. No. 07/922,277, filed Jul. 29, 1992 abandoned, which in turn is a continuation of application Ser. No. 07/643,876, filed Jan. 18, 1991, now abandoned.

This invention relates to a process for the production of highly pure 6-alpha-aminoacyl-penicillins and 7-alpha-aminoacyl-desacetoxy-cephalosporins which on the industrial scale is economical to operate, and is environmentally acceptable, avoiding the use of halogen-containing solvents such as methylene chloride.

Many processes have been investigated for the industrial production of 6-alpha-aminoacyl-penicillins and 7-alpha-aminoacyl-desacetoxy-cephalosporins. Such processes must meet the necessary criteria for adoption on a commercial scale e.g. high yield, economy and ease of operation, including easy and effective purification of the end product, and few reaction steps. Processes which have been operated commercially on a large scale have required the use of halogen-containing solvents such as methylene chloride, despite the fact that these solvents are difficult to recycle or dispose of in an environmentally acceptable manner. The 6-alpha-aminoacyl-penicillins and 7-alpha-aminoacyl-desacetoxy-cephalosporins produced also inevitably contain trace amounts of solvents and in the case of halogen-containing solvents such as methylene chloride, this is undesirable since there are fears that these could be carcinogenic.

In the literature there is no general or clear teaching of how varying reaction conditions, reactants, solvents or other factors in the synthesis of 6-alpha-aminoacyl-penicillins and 7-alpha-aminoacyl-desacetoxy-cephalosporins and their solvates affect yields, purity etc. This may be due to the fact that the penicillin and cephalosporin nucleus is very labile, several reactive moieties are present. The art is thus very empirical.

Ampicillin and amoxicillin, well known representatives of the class of 6-alpha-aminoacyl-penicillins are now produced industrially on the large scale using methylene chloride.

Ampicillin and amoxicillin are generally produced according to the so-called acid chloride process based on e.g. a D-phenyl-glycyl chloride hydrochloride as agent for acylating 6-APA, or according to the so-called Dane salt process wherein a salt of a D-phenyl-glycine having the amino group protected as an enamine is reacted with a reactive acid derivative such as a chloroformic acid ester or an organic acid chloride to form a mixed anhydride which is used to acylate 6-APA.

The acid chloride process involves use of an acid chloride hydrochloride which is highly reactive. Good yields are achieved in methylene chloride, especially when the beta-lactam nucleus is silylated. In the Dane salt process the best yields have also been previously obtained in methylene chloride.

For example, some syntheses of 6-alpha-aminoacyl-penicillins have been disclosed as follows:

In EP 1133, the highest yield given for the production of amoxicillin according to the Dane salt process in methylene chloride using silylated 6-APA is 82.7%.

In DOS 2520647, the yields for the synthesis of amoxicillin in a solvent mixture of methylene chloride/methyl isobutyl ketone are up to 78.7%, and for ampicillin tosylate 81.7%.

In DOS 2822876, the Dane salt of p-hydroxyphenylglycine is first silylated in methylene chloride and then reacted with 6-APA trimethylsilyl ester or the triethylamine salt of 6-APA. The yield of amoxicillin is 82.6%.

In DOS 2613172, the synthesis of ampicillin by the Dane salt process in acetone/water is described with a yield of 80–82%. The synthesis has the important disadvantage that the acetone must be removed under a vacuum at a low temperature before isolation of the active agent. On an industrial scale, the products are not stable and the quality of the products may not be satisfactory.

AT Patent 255647 describes an analogous synthesis, but the yields, calculated on activity, appear to be 66–72% and the ampicillin obtained is impure.

JP 54059296 describes the synthesis of amoxicillin in ethyl acetate. The penicillin nucleus is first silylated and a mixed anhydride formed from chloroformic acid ester and a Dane salt. The yield is low, 71.2%.

Methylene chloride is a widely used solvent because of its physical properties e.g. low boiling point, thus easy removal. Despite these advantages the use of methylene chloride and other halogen containing solvents have been criticised for years. Environmental problems arise in its use since methylene chloride is not biologically degradable. Emission controls on manufacturing plants using chlorinated hydrocarbons are contemplated. Various Pharmacopeia Commissions are considering the possibility of reducing methylene chloride residues in pharmaceuticals. The problem is especially acute for antibiotics since the proposed limits of 100–500 ppm residual methylene chloride is far exceeded in the case of antibiotics (usual values 1000 to 3000 ppm).

There was thus a clear need to find alternative industrially viable syntheses of 6-alpha-aminoacyl-penicillins and 7-alpha-aminoacyl-desacetoxy-cephalosporins. After exhaustive testing we have found a new synthesis for the production of these compounds which possesses a number of significant practical and economic advantages in industrial use. It uses only solvents which do not contain halogen atoms and are environmentally acceptable, gives high yields of at least 80 to 85 per cent or, in some cases, even over 90 per cent and produces highly pure products. It also obviates the need for equipment for generating vacuum, sealing and safety problems, which result from the use of acetone as solvent. Furthermore it is economical in operation and yet complicated purification techniques are avoided. The process is applicable to the synthesis of a wide variety of 6-alpha-amino-acyl-penicillins and 7-alpha-aminoacyl-desacetoxy-cephalosporins.

Accordingly in one aspect the present invention provides a process for the production of an 6-alpha-aminoacyl-penicillin or 7-alpha-aminoacyl-desacetoxy-cephalosporin without the use of halogen-containing solvent in a yield greater than 80% e.g. greater than 83 or 85% and in a purity at least 97.0%, e.g. at least 98%.

Accordingly in another aspect the invention provides a process for the production of an 6-alpha-aminoacyl-penicillin or 7-alpha-aminoacyl-desacetoxy-cephalosporin without the use of a halogen-containing solvent which comprises the steps of (i) producing a mixed carboxylic acid anhydride by reacting an N-substituted vinyl alpha-amino acid with an appropriate acylating agent in a solvent which does not contain halogen atoms and which is water-immiscible or sparingly soluble in water, and (ii) further reacting the resultant mixed carboxylic acid anhydride with 6-APA, 7-ADCA or a derivative thereof in a solvent which does not contain halogen atoms.

The process of the invention is useful for the preparation of a wide variety of 6-alpha-aminoacyl-penicillins and 7-alpha-aminoacyl-desacetoxy-cephalosporins, e.g. substituted 6-acetamidopenicillanic acid derivatives and 7-acetamido-3-desacetoxycephem-4-carboxylic acid derivatives. The acetamido group substituent may be for example phenyl, hydroxyphenyl or 1,4-cyclohexadien-1-yl.

For the purpose of this specification, the term "derivative" denotes e.g. analogues such as a compound which may bear a substituent at the amino group and/or wherein the carboxylic group is esterified.

Examples of a N-substituted vinyl alpha-amino acid are alpha-amino acids, wherein the amino group bears a protecting group as e.g. 1-methoxycarbonyl-propen-2-yl, 1-ethoxycarbonyl-propen-2-yl, 1-acetyl-propen-2-yl, 1-benzoyl-propen-2-yl, 1-(4-methoxy-benzoyl)-propen-2-yl or 1-(2,6-dimethoxy-benzoyl)-propen-2-yl.

The N-substituted vinyl alpha-amino acid can be employed as its salt. Examples of a salt are potassium, sodium, dicyclohexylammonium, N-methylpiperidinium or N-methylmorpholinium salts. Preferably salts are employed, more preferably Dane salts.

Examples of Dane salts suitable for the production of ampicillin, amoxicillin, epicillin or cephradine include sodium or potassium D-N-(1-methoxycarbonylpropen-2-yl)-α-aminophenylacetate, sodium or potassium D-N-(1-ethoxycarbonyl-propen-2-yl)-α-aminophenylacetate, sodium or potassium D-N-(1-methoxycarbonylpropen-2-yl)-α-amino-p-hydroxyphenylacetate, or sodium or potassium D-N-(1-ethoxycarbonyl-propen-2-yl)-α-amino-p-hydroxyphenylacetate, sodium or potassium D-N-(1-methoxycarbonylpropen-2-yl)-α-amino-2-(1,4-cyclohexadien-1-yl)-acetate.

The acylating agent is for example a reactive acid derivative of a $C_4$–$C_9$ acid. Suitable reactive derivatives include acid halides, e.g. an acid chloride. The acid may be an aliphatic, alicyclic, or aromatic acid. The acid may be for example an alkanoic acid such as pivalic acid or 2-ethylhexanoic acid. If desired the acid may contain an aromatic ring, e.g. benzoic acid. Preferred acylating agents are pivaloyl chloride, 2-ethyl-hexanoyl chloride and benzoyl chloride. Alternatively the acylating agent may be a chloroformic acid alkyl ester, e.g. ethyl chloroformate.

The formula of the mixed anhydride is preferably as follows:

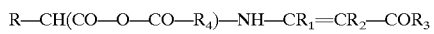

$$R-CH(CO-O-CO-R_4)-NH-CR_1=CR_2-COR_3 \quad I$$

wherein

R is an appropriate side chain, e.g. phenyl, 4-hydroxyphenyl or 1,4-cyclohexadien-1-yl $R_1$ is a $(C_{1-3})$alkyl group, preferably methyl, $R_2$ is hydrogen or $(C_{1-3})$alkyl group, preferably hydrogen, $R_3$ is a $(C_{1-4})$alkyl group, preferably methyl or ethyl; a $(C_{1-4})$alkoxy group, preferably methoxy or ethoxy; phenyl optionally substituted by alkoxy, $R_4$ is an aliphatic, alicyclic, or aromatic group, e.g. a $(C_{3-8})$alkyl group, or preferably phenyl or 1-ethylpentyl, or especially tert-butyl, and preferably wherein the amino group and the carbonyl group attached to the double bond have the cis configuration.

A small amount of a free $C_4$–$C_9$ acid may also be present in the production of the mixed anhydride. The acid is for example a $C_4$–$C_9$ acid. The acid may be for example an alkanoic acid such as pivalic acid or 2-ethylhexanoic acid. If desired the acid may contain an aromatic ring, e.g. benzoic acid.

The side chain of the free acid may be the same or different to that of the acylating agent. The preferred free acid is 2-ethylhexanoic acid or pivalic acid.

As indicated above in step i) there are used solvents which do not contain any halogen atoms. The term "sparingly soluble" includes solvents which are insoluble or slightly soluble in water. Examples of such solvents which are water-immiscible or sparingly soluble in water include those of low dielectric constant, e.g. appropriate ketones, esters and aromatic hydrocarbons. Examples include methyl-$(C_{2-4})$alkyl-ketones, such as methyl isobutyl ketone (hereinafter MIBK), di-$(C_{2-4})$alkyl-ketones, $(C_{1-3})$alkanoic acid butyl esters such as n-butyl acetate (hereinafter NBA) or iso-butyl acetate (hereinafter IBA), and toluene. Preferred solvents include MIBK, NBA and IBA.

Naturally the solvent system used in step i) may contain more than one solvent, provided that halogen-containing solvents are not used.

The solvent used in the formation of the mixed anhydride step may comprise one or more solvents, provided that the system as a whole is water-immiscible or sparingly soluble in water.

Thus if desired a small amount of a co-solvent may be present in step 1) which improves or activates the reaction of a Dane salt with the acid halide or other acylating agent.

We prefer the use of an organic amide such as a formamide or an acetamide, or their N-Mono or N,N-dimethyl derivatives, e.g. dimethyl formamide, or preferably N-methylacetamide, N,N-dimethylacetamide, or N-methylpyrrolidine or tetramethylurea.

Preferably a base, e.g. a tertiary amine base, is present as a catalyst for mixed carboxylic acid anhydride formation. Preferred catalysts include pyridines, for example a picoline, e.g. 3- or 4-picoline, or a lutidine.

The formation of the mixed carboxylic acid anhydride may be effected, e.g. at temperatures, from −50° to 50° C., and preferably from −40° to 0° C.

The product of step i) is generally a solution or a suspension of the mixed carboxlic acid anhydride which can be used further as such. If desired this anhydride may be maintained between step i) and step ii) at from ca. −60° to −20° C.

The step ii) is an acylation reaction of 6-APA or 7-ADCA which is preferably in salt form.

Conveniently a solution of the salt of 6-APA, 7-ADCA or derivative thereof is added to the reaction mixture resulting from the mixed carboxylic acid anhydride formation. Alternatively N-silylated 6-APA or 7-ADCA may be employed.

Thus the solvents indicated above as preferably used for the mixed carboxylic acid anhydride formation are also conveniently present in the acylation step.

The salt of 6-APA, 7-ADCA or derivative thereof is preferably in a solution or suspension in an organic solvent miscible with the solvent system used in the mixed carboxylic acid anhydride step and not containing halogen atoms.

The solvent system used for dissolving or suspending the salt of 6-APA, 7-ADCA or derivative thereof is preferably an alkanol, e.g. $(C_1$–$C_4)$alkanol, e.g. ethanol, and preferably a $(C_{3-4})$alkanol, e.g. butanol or especially isopropanol, optionally in combination with a solvent used in step i).

If desired a small amount of water may be present, especially when 6-APA is being used.

If desired small amounts $(C_{4-9})$alkanoic acid e.g. 2-ethylhexanoic acid may be added to the mixture of the salt of 6-APA, 7-ADCA or derivative thereof and solvent.

Preferred salts of penicillins and cephalosporins include secondary or tertiary amine salts. Preferred salts for 6-APA or derivative thereof include secondary or tertiary amines containing up to 6 carbon atoms, e.g. $(C_{1-4})$alkylamines such as diethylamine, di-isopropylamine, triethylamine, diisopropylethylamine (Hunig's base), tributylamine and preferably triethylamine. Preferred salts for 7-ADCA or derivative thereof include 1,8-diazabicyclo[5,4,0]undec-7-ene or tetramethylguanidine as described e.g. in U.S. Pat. Nos. 4,405,782 and 4,659,814.

Suitable reaction temperatures for the acylation step may be from about −60° C. to room temperature, preferably at or under −15° C.

The reaction mixture of the acylation step may be worked up in conventional manner. The protected 6-alpha-aminoacyl-penicillin or 7-alpha-aminoacyl-desacetoxy-cephalosporin may be deprotected using known methods. The substituted vinyl group may be split by hydrolysis in aqueous acid.

The final product may be isolated in conventional manner, by adjusting pH. Purity may be very high, e.g. above 98%. The isolated product may contain traces of solvent residues, but is free from halogen-containing solvent.

In another aspect the invention relates to the first step of the process previously described, namely a process for the production of a mixed carboxylic acid anhydride of a N-substituted vinyl alpha-amino acid, without the use of a halogen-containing solvent, characterised by reacting a N-substituted vinyl alpha-amino acid with an appropriate acylating agent in a solvent which does not contain halogen atoms and which is water-immiscible or sparingly soluble in water.

In a preferred embodiment the invention provides a process for the production of a 7-alpha-aminoacyl-desacetoxy-cephalosporin without the use of a halogen-containing solvent which comprises the steps of i) producing a mixed acid anhydride by reacting a N-substituted vinyl alpha-amino acid with an appropriate acylating agent in a solvent which does not contain halogen atoms and which is water-immiscible or sparingly soluble in water, and (ii) further reacting the resultant mixed acid anhydride with a salt of 7-ADCA or derivative thereof in a solvent which does not contain halogen atoms.

Insofar as the production of any starting material used in the process of the invention, e.g. the Dane salt, is not particularly described herein this is known or may be made in analogous manner to known processes.

The following non-limitative examples illustrate the invention. All temperatures are in degrees Centigrade and are uncorrected.

In the examples the following abbreviations are used:

| | |
|---|---|
| NBA = | n-butyl acetate |
| IBA = | isobutyl acetate |
| IPA = | isopropanol |
| MIBK = | Methyl isobutyl ketone |
| Dane salt A = | Potassium D-N-(1-ethoxycarbonylpropen-2-yl)-α-aminophenylacetate |
| Dane salt B = | Potassium D-N-(1-methoxycarbonylpropen-2-yl)-α-amino-p-hydroxyphenylacetate |
| Dane salt C = | Sodium D-N-(1-methoxycarbonylpropen-2-yl)-α-amino-2-(1,4-cyclohexadien-1-yl)acetate |
| DBU = | 1,8-diazabicyclo[5,4,0]undec-7-ene |

The yield given is based on 6-APA or 7-ADCA used as starting material. Purity is measured by HPLC on anhydrous basis.

The examples illustrate in step i) the mixed carboxylic acid anhydride formation, in step ii) the acylation of the beta-lactam using the mixture obtained in step i) without isolation, and in step iii) working up, including deprotection, to give the product.

EXAMPLE 1

Ampicillin Trihydrate i) 0.03 ml 4-picoline are added to a suspension of 61.3 g Dane salt A in 124.9 ml NBA. The resultant mixture is stirred for 15 minutes at room temperature and cooled to −33°; 24.1 ml pivaloyl chloride are added. The resultant milky, greenish suspension is stirred at −20° for 90 minutes and cooled to −45° giving a mixture containing the mixed carboxylic acid anhydride.

ii) 40 g 6-APA are dissolved in a mixture of 48.6 ml IPA, 10.4 ml water and 29.4 ml triethylamine, and this solution is added dropwise to the mixture obtained in step i) at a temperature of −45° to −30° over 45 minutes and the reaction mixture is stirred for a further 90 minutes at a temperature of −30° to −35°.

iii) The resultant crude protected ampicillin mixture is worked up by treating with a mixture of 289 ml ice-water and 39.6 ml concentrated HCl and stirred for 30 minutes while cooling with ice. The aqueous phase is separated off and the organic phase back-extracted with a mixture of 5.4 ml concentrated HCl and 44.5 ml water. The combined aqueous phases are filtered through a filtering aid and pumped into a suspension of 5 g ampicillin trihydrate seed crystals in 100 ml water keeping the pH from 4.5 to 5.0 by the addition of concentrated aqueous ammonia. The title compound is obtained by standing the mixture overnight in a refrigerator, isolating the crystals, and washing them with 60 ml ice-water and 3×50 ml 90% acetone, followed by drying. Yield 61.6 g=82.4%, Purity 98.8%.

EXAMPLE 2

Ampicillin Trihydrate i) 0.03 ml 4-picoline and 0.51 g pivalic acid are added to a suspension of 60.2 g Dane salt A in 128.6 ml NBA. The resultant mixture is stirred for 5 minutes at room temperature and cooled to −30° C.; 24.1 ml pivaloyl chloride are added. The mixture is stirred for 60 minutes at −20°. A solution of 5.1 g pivalic acid in 14.3 ml of NBA is added. The reaction mixture containing the mixed carboxylic acid anhydride is cooled to −45° C.

ii) 40 g 6-APA are dissolved in a mixture of 48.6 ml IPA, 10.3 ml water and 31.4 ml triethylamine, and this solution is added dropwise to the mixture obtained in step i) at a temperature of −45° to −40° over 30 minutes and the reaction mixture is stirred for a further 90 minutes at a temperature of −30° to −35°.

iii) The resultant crude protected ampicillin mixture is worked up by treating with a mixture of ice-water and concentrated HCl. After phase separation the aqueous phase is brought to pH 4.5. The title compound is obtained after filtration and washing with 90% aqueous acetone, followed by drying. Yield 66.34 g=89%. Purity 98.8%.

Example 2 is repeated with the following changes:

a) The same quantity of isobutylacetate is used instead of NBA in step i). Yield 65.4 g=88%. Purity 98.9%.

b) The same quantity of 3,5-lutidine is used instead of 4-picoline and the same quantity of isobutylacetate is used instead of NBA in step i). Yield 65.0 g=87%. Purity 98.6%.

c) The same quantity of tert. butylacetate is used instead of NBA in step i). Yield 64.1 g=86%. Purity 99.0%.

d) The same quantity of isopropylacetate is used instead of NBA in step i). Yield 65.9 g=88%. Purity 98.7%.

e) The same quantity of 2-ethylhexanoic acid is used instead of pivalic acid in step i). Yield 65.2 g=87.0%. Purity 99.1%.

EXAMPLE 3

Ampicillin Trihydrate i) 0.035 ml 4-picoline are added to a suspension of 62.1 g Dane salt A in 150 ml MIBK. 24.5 ml pivaloyl chloride are added dropwise maintaining a temperature of from −12° to −15°. The mixture is stirred for a further 20 minutes at −15° and then cooled to −35° giving a mixture containing the mixed carboxylic acid anhydride.

ii) 0.8 ml 2-ethylhexanoic acid are added to 40 g 6-APA in a mixture of 25 ml MIBK, 25 ml IPA, 14 ml water and 29.3 ml triethylamine, and this mixture is added dropwise to the mixture of the mixed anhydride obtained in step i) at such a rate that the temperature does not exceed −25°. The resultant mixture is stirred for 90 minutes at −30°.

iii) The mixture of step ii) is brought to 0° and then added to a mixture of 400 ml ice-water and 35 ml concentrated HCl and is kept under 5° for 30 minutes. The phases are divided and the acidic aqueous phase is treated slowly with concentrated aqueous ammonia to bring the pH to 4.8. The title compound separates out, is collected by filtering and washing, followed by drying as in Example 1. Yield 63.1 g=83%. Purity 99%

EXAMPLE 4

Amoxicillin Trihydrate i) 78.1 kg Dane salt B are added to 200 liters MIBK. 33.7 kg N,N-dimethylacetamide are then added followed by 175 ml 3-picoline and then 1.4 liters 2-ethylhexanoic acid. The resultant suspension is stirred for 15 minutes at 20° to 22° and then cooled to −30° C. 30.8 liters pivaloyl chloride are added. The mixture is stirred for 60 minutes at −13° to −20° and then cooled to −45° to give a mixture containing the mixed carboxylic acid anhydride.

ii) 50 kg 6-APA is added to 62.5 liters IPA, 13 liters water and 36.8 liters triethylamine in a reaction vessel. The mixture, a thin suspension, is added to the mixture obtained in step i) at −34° to −40°. The reaction vessel which contained the 6-APA suspension is washed with 20 liters MIBK and the washings added to the reaction mixture. The acylation is allowed to proceed for 90 minutes at −30° to −35°.

iii) The reaction mixture from step ii) is added to a mixture of 653 liters water and 50 liters concentrated HCl. The acylation vessel is washed with 30 liters MIBK and the washings added to the aqueous mixture. The two phase mixture is stirred for 10 minutes at 5° and the phases divided. The aqueous phase containing the title compound is filtered and continuously pumped into a suspension of 120 liters water containing 3.1 kg amoxicillin seed crystals keeping the pH value between 4 and 5 by the addition of concentrated aqueous ammonia at a temperature about 10°. The crystalline suspension is allowed to stand overnight. The title compound is centrifuged off and washed and dried as in Example 1. Yield 81.7 kg=84.1%. Purity 100%.

EXAMPLE 5

Amoxicillin Trihydrate i) 312.6 g Dane salt B are added to a mixture of 1000 ml NBA and 71 ml N,N-dimethylacetamide. 0.7 ml 3-picoline and then 2.6 g pivalic acid are added and the resultant suspension cooled to −30°. 123 ml pivaloyl chloride are added and the mixture stirred for 1 hour at −20°. 25.6 g pivalic acid are added and the suspension cooled to −50° to give a mixture containing the mixed carboxylic acid anhydride.

ii) A solution of 200 g 6-APA in a mixture of 240 ml IPA, 147 ml triethylamine and 60 ml water is added dropwise to the mixture obtained in step i) keeping the temperature between −50° and −35°. The mixture is stirred then for 90 minutes at −35°.

iii) The mixture is worked up in analogous manner to Example 4. Yield 343.7 g=88.5%. Purity 97.7%.

Example 5 is repeated with the following changes:

a) The same quantity of MIBK is used instead of NBA in step i). Yield 333.8 g=87.3%. Purity 98.7%.

b) The same quantity of 2-ethylhexanoic acid is used instead of pivalic acid. Yield 87.1%. Purity 97.7%.

c) As for b) but using the same quantity of MIBK instead of NBA. Yield 86.5%. Purity 97.9%.

d) No addition of pivalic acid. Yield 86.4%. Purity 98.2%.

EXAMPLE 6

Cephradine i) 9.26 g Dane Salt C, 46 ml NBA, 0.74 g N-methylacetamide and 0.002 ml 4-picoline are mixed and the mixture is cooled to −20 to −25°. 3.74 ml benzoyl chloride are added. The mixture is stirred for 1 hour at −20° to −25°, and cooled to −55° to give a mixture containing the mixed carboxylic acid anhydride.

ii) 6 g 7-ADCA, 11 ml NBA and 11 ml IPA are mixed at 20° to 25°. The mixture is cooled to 10°. 4.59 ml DBU are added. The mixture is stirred for 15 minutes at 20° to 25° to give a yellow solution, which is added dropwise to the mixture obtained in step i) over about 20 minutes at −50° to −55°. The mixture is stirred for 3 hours at −40°/−30°.

iii) The mixture is worked up in analogous manner to Example 2. Yield 8.65 g=84.1%. Purity 99.5%.

EXAMPLE 7

Cephalexin Monohydrate i) 10.01 g Dane Salt A, 45 ml NBA and 0.0046 ml 4-picoline are mixed and reacted with benzoyl chloride in analogous manner to Example 6 step i).

ii) 6 g 7-ADCA are reacted with 3.69 ml tetramethylguanidine instead of DBU in analogous manner to Example 6 step ii) and reacted analogously with the mixture from step i).

iii) Vorking up is effected in analogous manner to Example 6 step iii). Yield 8.82 g=86.2%. Purity 99.0%.

EXAMPLE 8

Cefadroxil i) 10.47 g Dane Salt B, 25 ml NBA, 28 ml dimethylformamide, 0.096 ml 4-picoline are mixed and the mixture cooled to −25° to −30°. 3.77 ml benzoyl chloride are added and the mixed carboxylic acid anhydride produced in analogous manner to Example 6 step i).

ii) 6 g 7-ADCA and 11 ml IPA are mixed at 20° to 25°. The mixture is cooled to 10°. 3.69 ml tetramethylguanidine are added and the solution stirred for 5 minutes at 20° to 25° to give a yellow solution. 11 ml NBA are added and this mixture is added dropwise to the mixture obtained in step i) in analogous manner to that described in Example 6 step ii). Acylation is effected in analogous manner to Example 6 step ii). EPLC analysis of the mixture gives a Cefadroxil yield of greater than 85%.

iii) The mixture is worked up in analogous manner to Example 1 and allows the isolation of Cefadroxil dimethylformamide solvate. This solvate is transformed in Cefadroxil by treatment in aqueous methanol. Purity of isolated product 99.2%.

EXAMPLE 9

Epicillin i) 0.005 ml 4-picoline and 0.09 g pivalic acid are added to a suspension of 9.8 g Dane salt C in 22.5 ml NBA. The resultant mixture is cooled to −20°; 4.44 ml pivaloyl chloride are added. The mixture is stirred for 60 minutes at −10°. A solution of 0.895 g pivalic acid in 2.5 ml NBA is added. The reaction mixture containing the mixed carboxylic acid anhydride is cooled to −45° C.

ii) 7 g 6-APA are dissolved in a mixture of 17 ml IPA, 3.6 ml water and 11 ml triethylamine, and this solution is added dropwise to the mixture obtained in step i) at a temperature of −45° to −40° over 30 minutes and the reaction mixture is stirred for a further 90 minutes at a temperature of −30° to −35°. HPLC gives an Epicillin yield of greater than 85%.

iii) The mixture is worked up in analogous manner to Example 1. Purity of isolated product 99.0%.

What we claim is:

1. In a process for the preparation of a 6-α-aminoacyl-penicillin derivative or a 7-α-aminoacyl-desacetoxy-cephalosporin derivative comprising the steps of
   i) preparing a mixed carboxylic acid anhydride by reacting an N-substituted-vinyl-α-amino acid or a salt thereof with an acylating agent,
   ii) reacting the obtained mixed carboxylic acid anhydride with 6-APA, 7-ADCA or a derivative of 6-APA or 7-ADCA, in free acid or salt form, and
   iii) isolating the product,
the improvement which comprises carrying out
   step i) in a solvent which does not contain any halogen atoms and which is water-immiscible or sparingly soluble in water or a mixture of such solvents,
   step ii) in a solvent which does not contain any halogen atoms or a mixture of such solvents and with 6-APA, 7-ADCA or a non-silylated derivative of 6-APA or 7-ADCA, in free acid or salt form and
   step iii) by adjusting the pH to obtain the product in a yield greater than 80% and a purity of at least 97.0%, the product being free from halogen-containing solvent.

2. A process according to claim 1 wherein step ii) is carried out by mixing a solution or suspension of a salt of 6-APA, 7-ADCA or a derivative thereof in an $(C_{3-4})$alkanol with the mixed carboxylic acid anhydride.

3. A process according to claim 1 wherein step i) is carried out in the presence of a picoline or a lutidine.

4. A process according to claim 1 wherein the acylating agent is a reactive acid derivative of a $C_4$–$C_9$alkanoic acid or benzoic acid.

5. A process according to claim 4 wherein the acylating agent is pivaloyl chloride, 2-ethylhexanoyl chloride or benzoyl chloride, and the acylation is effected in the presence of a free $(C_{4-9})$ carboxylic acid.

6. A process according to claim 1 wherein an ester or a ketone.

7. A process according to claim 6 wherein step i) is carried out in n-butyl acetate.

8. A process according to claim 5 wherein step i) is carried out in a solvent comprising methyl isobutyl ketone.

9. A process according to claim 1 wherein the mixed carboxylic acid anhydride is produced in the presence of an amide.

10. A process according to claim 1 for the production of ampicillin or amoxicillin wherein in step i) there is produced a mixed carboxylic acid anhydride of the formula $$p-H(O)_m-C_6H_4-CH(CO-O-R^1_4-NH-CR_1=CR_2-CO-R^1_3,$$

wherein
   $R_1$ is $(C_{1-3})$alkyl,
   $R_2$ is hydrogen or $(C_{1-3})$alkyl,
   $R^1_3$ is $(C_{1-4})$alkoxy,
   $R^1_4$ is $(C_{3-8})$alkyl, and
   m is 0 or 1,
and wherein the —NH— and —CO— radicals attached to the double bond have the cis configuration, and in step ii) the mixed carboxylic acid anhydride is reacted with a solution of a salt of 6-APA with a secondary or tertiary amine, and the product is isolated by treating with aqueous acid followed by base.

11. A process according to claim 10 wherein the mixed carboxylic acid anhydride is produced by reacting a Dane salt with a $(C_{4-9})$alkanoic acid chloride in the presence of a pyridine derivative in a solvent selected from an acetic acid $(C_{1-4})$alkyl ester and a $(C_{4-6})$ketone, or a mixture thereof, and in step ii) the mixture obtained from step i) is reacted with a solution of a salt of 6-APA with a secondary or tertiary $(C_{1-6})$alkyl amine in a solvent selected from an acetic acid $(C_{1-4})$alkyl ester and a $(C_{4-6})$ketone, alone or in the presence of water, a $(C_{1-4})$alcohol, a $(C_{1-4})$alcohol/water mixture or a mixture of any of the preceding solvents, and the product is isolated by treating with aqueous acid.

12. A process according to claim 10 wherein pivaloyl chloride is used to form the mixed carboxylic acid anhydride.

13. A process according to claim 10 wherein a picoline or lutidine is used in step i).

14. In a process for the preparation of a 6-α-aminoacyl-penicillin derivative or a 7-α-aminoacyl-desacetoxy-cephalosporin derivative comprising the steps of
   i) preparing a mixed carboxylic acid anhydride of the formula $$R-CH(CO-O-CO-R_4)-NH-CR_1=CR_2-COR_3,$$

wherein R is phenyl, 4-hydroxyphenyl or 1,4-cyclohexadien-1-yl,
   $R_1$ is $(C_{1-3})$alkyl,
   $R_2$ is hydrogen or $(C_{1-3})$alkyl,
   $R_3$ is $(C_{1-4})$alkyl, $(C_{1-4})$alkoxy or phenyl, and
   $R_4$ is $(C_{3-0})$alkyl or phenyl,
by reacting a sodium, potassium, dicyclohexylammonium, N-methyl-piperidinium or N-methylmorpholinium salt of a compound of the formula $$R-CH(COOH)-NH-CR_1=CR_2-COR_3$$

with a reactive acylating derivative of an acid of the formula $$R_4-COOH$$

wherein R, $R_1$, $R_2$, $R_3$ and $R_4$ are as defined above,
   ii) reacting the obtained mixed carboxylic acid anhydride with 6-APA, 7-ADCA or a non-silylated derivative of 6-APA or 7-ADCA, in free acid or salt form, and
   iii) isolating the product,
the improvement which comprises carrying out
   step i) in a non-halogenated solvent selected from the group consisting of methyl isobutyl ketone, n-butyl acetate, isobutyl acetate and iso-propyl acetate, step ii) in a non-halogenated solvent selected from methyl isobutyl ketone and isopropyl alcohol, alone or mixed with the solvent of step i), and step iii) by splitting off $HCR_1=CR_2-COR_3$ by hydrolysis in aqueous acid and adjusting the pH to 4 to 5 to obtain the product in a yield of at least 80% and a purity of at least 97.0%.

15. A process according to claim 1 wherein the mixed carboxylic acid anhydride is prepared by reacting a Dane salt with an acylating agent.

16. A process according to claim 15 wherein the Dane salt is selected from sodium and potassium D-N-(1-methoxycarbonylpropen-2-yl)-α-aminophenylacetate, D-N-(1-ethoxycarbonylpropen-2-yl)-α-aminophenylacetate, D-N-(1-methoxycarbonylpropen-2-yl)-α-amino-p-hydroxy-phenylacetate, D-N-(1-ethoxycarbonylpropen-2-yl)-α-amino-p-hydroxyphenyl acetate, and D-N-(1-methoxycarbonylpropen-2-yl)-α-amino-2-(1,4-cyclohexadien-1-yl)acetate.

17. A process according to claim 2 wherein the $(C_{3-4})$ alkanol is isopropanol.

18. A process according to claim 1 wherein the triethylamine salt of 6-APA or a non-silylated derivative thereof or the tetramethylguanidine or 1,8-diazabicyclo[5.4.0]undec-7-ene salt of 7-ADCA or a nonderivative thereof is used in step ii).

* * * * *